United States Patent [19]
Walle

[11] Patent Number: 5,584,303
[45] Date of Patent: Dec. 17, 1996

[54] THERAPEUTIC LEG SUPPORT

[76] Inventor: Alexander J. Walle, 314 W. 58th St. #2B, New York, N.Y. 10019

[21] Appl. No.: 545,064

[22] Filed: Oct. 19, 1995

[51] Int. Cl.$^6$ ............................................. A61G 15/00
[52] U.S. Cl. ........................... 128/845; 128/882; 5/648; 5/651
[58] Field of Search ............................ 128/845, 846, 128/869, 882; 602/5, 8, 13, 14, 15; 5/648, 650, 651

[56] References Cited

U.S. PATENT DOCUMENTS

| | | | |
|---|---|---|---|
| 3,511,233 | 5/1970 | Holy | 5/651 |
| 3,901,228 | 8/1975 | Brown | 128/882 |
| 3,946,451 | 3/1976 | Spann | 5/650 |
| 5,046,487 | 9/1991 | Scott | 5/650 |

*Primary Examiner*—Michael A. Brown
*Attorney, Agent, or Firm*—Sprung Horn Kramer & Woods

[57] ABSTRACT

A therapeutic leg elevator having a first open-topped portion contoured to support the leg of a patient from approximately the ankle to at least the calf of the patient, and a foot portion connected approximately to the perpendicularly horizontal portion, the foot portion having an opening facing the horizontal portion so as to receive the patient's foot, the opening having a base which the patient's foot sole may contact, the opening being contoured below the patient's heel so the heel does not contact the foot portion, the opening extending upwardly beyond the end of the patient's toes and being upwardly bounded by a protective cover which is part of said foot portion, whereby the tops of the patient's toes and bottom of his heel, and optionally the sole of his foot, are protected while said foot portion is supported.

6 Claims, 1 Drawing Sheet

U.S. Patent : Dec. 17, 1996 : 5,584,303
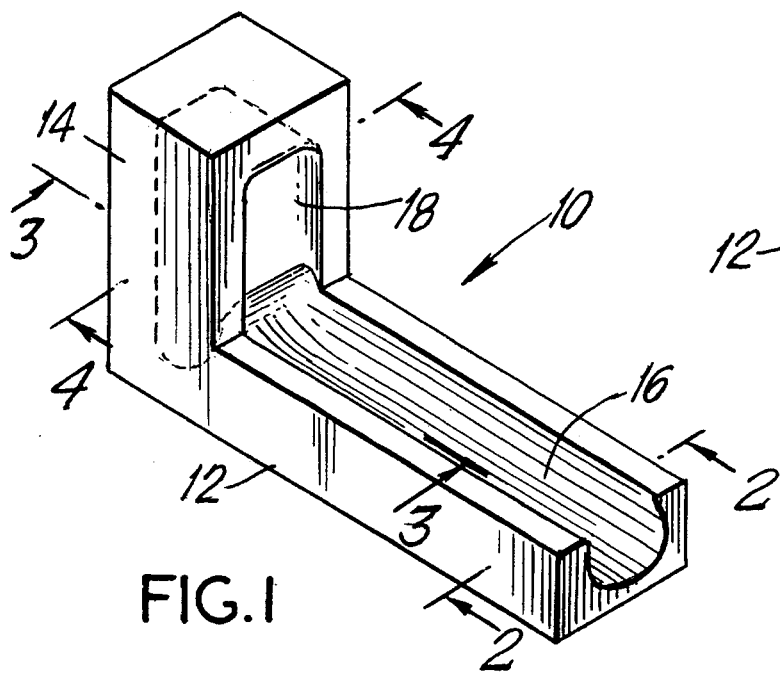
FIG.1  FIG.2
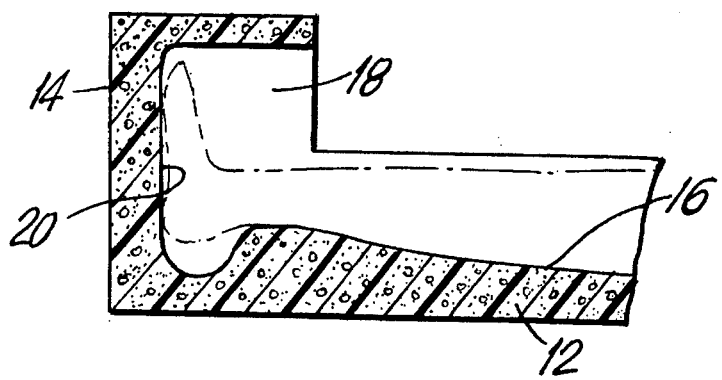
FIG.3
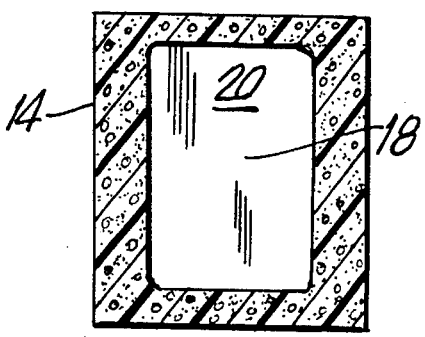 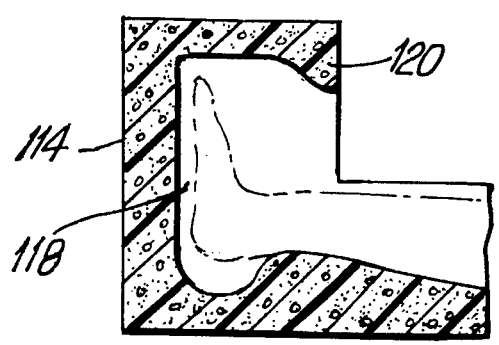
FIG.4  FIG.5

THERAPEUTIC LEG SUPPORT

The invention relates to a novel therapeutic leg support.

For certain leg problems it is necessary to support a patient's foot. In some instances it is important that the toes and/or heel and even the sole be free to heal or mend without weight being placed upon them.

Various leg supports have been provided for these purposes with varying degrees of success. For example, such devices are shown in U.S. Pat. Nos.

3,162,486
3,511,233
3,946,451
4,071,031
4,135,504
4,186,738
4,779,296
5,046,487
5,125,123
5,289,828.

It is an object of the present invention to provide an extremely simple support to serve these purposes and which is easy to manufacture, store, put into place and use with maximum patient benefit and comfort.

These and other objects and advantages are realized in accordance with the present invention, pursuant to which there is provided a therapeutic leg elevator comprising a first open-topped portion contoured to support the leg of a patient from approximately the ankle to at least the calf of the patient and a foot portion connected approximately perpendicularly to the horizontal portion, the foot portion having an opening facing the horizontal portion so as to receive the patient's foot, the opening having a base which the patient's foot sole may contact, the opening being contoured below the patient's heel so the heel does not contact the foot portion, the opening extending upwardly beyond the end of the patient's toes and being upwardly bounded by a protective cover which is part of said foot portion, whereby the tops of the patient's toes and bottom of his heel, and optionally the sole of his foot, are protected while said foot portion is supported.

Advantageously the sides of the elevator which contact the patient's leg between ankle and knee are contoured to grab the leg lightly. The top opening through which the leg enters the channel between side walls in temporarily enlarged by pulling on the elastic flexible side walls, release effecting their restoration to initial positions. The high ankle area to the low knee are, in conjunction with the circular comprehension of the leg (afforded by the flexible side walls) distinguishing from the ankle area to the knee area, provides a simple means to prevent various stages and dependent edema, thus preventing the circulation in the limb from deteriorating during immobilization.

Further the leg support slopes down, such sloping down from the high ankle area to the low knee area, in conjunction with the circular compression of the leg (afforded by the flexible side walls) diminishing from the ankle area to the knee area, provides a simple means for preventing venous stasis and dependent edema, thus preventing the circulation in the limb from deteriorating during immobilization.

Advantageously the horizontal and vertical portions are integral with one another, part of a single molding. The molded article is relatively stiff so as to maintain its shape even with a leg resting on it. A stiff light-weight material such as foamed polyurethane or foamed polystyrene is quite suitable.

It can be open-cell or closed-cell foam, the former permitting air flow therethrough.

In other embodiments, the foot and leg portions can be separately molded and joined to one another by bonding or mechanical attachment. The molding can be of a plastic such as polyethylene.

Different supports can be provided for a left foot and a right foot but generally a single support will be adequate for either foot. Similarly, the support can come in different sizes to accommodate legs and feet of different sizes. However, if a somewhat long support is provided, if made out of material such as foamed plastic it can easily be shortened by transverse cutting with a knife or saw.

The invention will now be further described with reference to the accompanying drawings wherein:

FIG. 1 is a perspective view of one embodiment of a leg support in accordance with the invention;

FIG. 2 is a section taken on line 2—2 of FIG. 1;

FIG. 3 is a longitudinal section taken on line 3—3 of FIG. 1;

FIG. 4 is a section taken on line 4—4 of FIG. 1; and

FIG. 5. is a partial longitudinal sectional view of another embodiment in accordance with the present invention.

Referring now more particularly to the drawing, in FIG. 1 there is shown a leg support 10 comprising a generally horizontal portion 12 and integral therewith a generally vertical portion 14. As best seen in FIG. 2, the portion 12 in conventional manner has an open topped depression 16 which is contoured to the leg of a patient from approximately the ankle to at least the calf (see FIG. 3).

As seen in FIG. 3, the portion 14 has an opening 18 continuous with depression 16 but of a special configuration. The opening 18 is of a size and shape to encircle the patient's foot and to protect it but not to pressure it. Thus the floor 20 of the opening 18 might be of a size so that the sole of the foot can contact it, or it may be dimensioned so as to be spaced from the sole.

FIG. 4 is a transverse vertical section at the location in FIG. 3 just below the patient's heel.

Thus the patient's foot is positively supported from at least the calf to the ankle. Therebelow the foot is largely unsupported but yet the toes, sole and heel are protected from external factors, i.e. physically shielded.

In the embodiment of FIG. 5, the vertical portion 114 has an opening 118 of somewhat different configuration. The opening has an overhanging portion 120 to maximize protection for the foot. While the mouth of the opening is smaller than in the first embodiment, its size is somewhat larger so that none of the heel, sole or toes contacts the portion 14.

It will be understood that the specification and examples are illustrative but not limitative of the present invention and that other embodiments within the spirit and scope of the invention will suggest themselves to those skilled in the art.

I claim:

1. A therapeutic leg elevator comprising a horizontal portion having a first open-topped portion contoured to support the leg of a patient from approximately the ankle to at least the calf of the patient, and a foot portion connected approximately perpendicularly to the horizontal portion, the foot portion having an opening facing the horizontal portion so as to receive the patient's foot, the opening having a base which the patient's foot sole may contact, the opening being contoured below the patient's heel so the heel does not contact the foot portion, the opening extending upwardly beyond the end of the patient's toes and being upwardly bounded by a protective cover which is part of said foot portion, whereby the tops of the patient's toes and bottom of his heel, and optionally the sole of his foot, are protected while said foot portion is supported.

2. A leg elevator according to claim 1, formed of stiff light weight material.

3. A leg elevator according to claim 1, formed of foamed plastic.

4. A leg elevator according to claim 1, wherein the first portion slopes downwardly from the ankle area toward the knee area.

5. A leg elevator according to claim 1, wherein the leg portion is contoured so as lightly to grab the leg of a patient positioned therein.

6. A leg elevator according to claim 5, wherein the first portion shapes downwardly from the ankle area toward the knee area, the elevator being formed of flexible stiff light weight foamed plastic.

* * * * *